(12) United States Patent
Gallagher et al.

(10) Patent No.: US 7,528,277 B2
(45) Date of Patent: May 5, 2009

(54) METHOD TO PRODUCE A CARBOXYLIC ACID ESTER FROM A CARBOXYLIC ACID AMMONIUM SALT BY ALCOHOLYSIS

(75) Inventors: F. Glenn Gallagher, Wilmington, DE (US); Robert DiCosimo, Chadds Ford, PA (US)

(73) Assignee: E.I. DuPont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/315,708

(22) Filed: Dec. 21, 2005

(65) Prior Publication Data

US 2006/0189821 A1  Aug. 24, 2006

Related U.S. Application Data

(60) Provisional application No. 60/638,126, filed on Dec. 22, 2004.

(51) Int. Cl.
C07C 67/00 (2006.01)
C07C 69/66 (2006.01)
C07C 69/02 (2006.01)

(52) U.S. Cl. .......................... 560/77; 560/179; 560/231

(58) Field of Classification Search .................. 560/77, 560/179, 231
See application file for complete search history.

(56) References Cited

U.S. PATENT DOCUMENTS

| 2,565,487 | A |  | 8/1951 | Filachione et al. |
|---|---|---|---|---|
| 3,935,238 | A | * | 1/1976 | Norton .......................... 560/80 |
| 4,055,590 | A | * | 10/1977 | Gruber et al. ................ 560/179 |
| 6,291,708 | B1 |  | 9/2001 | Cockrem |
| 6,383,786 | B1 |  | 5/2002 | Chauhan et al. |
| 6,416,980 | B1 |  | 7/2002 | Chauhan et al. |
| 2004/0138409 | A1 |  | 7/2004 | Hayashi et al. |
| 2004/0210087 | A1 |  | 10/2004 | Xiangsheng et al. |

FOREIGN PATENT DOCUMENTS

WO   WO 2004052818 A1 * 6/2004

OTHER PUBLICATIONS

G. Ondrey, Pushing Propylene Production, Chemical Engineering, 2004, pp. 20-23, vol. 20.
Robert H. Perry et. al. Perry's Chemical Handbook, 7$^{TH}$ Edition, McGraw Hill Companies, New York, NY, 1997 (Book Not Included).
J. Gurthrie et. al., Effect of the ACYL Substituent on the Equilibrium Constant for Hydration of Esters, Can J. Chem., pp. 1281-1294, vol. 58.
Wasewar et. al., Reactive Extraction of Lactic Acid Using Alamine 336 in MIBK: Equilibria and Kinetics, J. Biotechnol., 2002, pp. 59-68, vol. 97.
M. Filachione et. al., Preparation of Esters by Reaction of Ammonium Salts With Alcohols, Journal of the American Chemical Society, 1951, pp. 5265-5267, vol. 73.

* cited by examiner

*Primary Examiner*—Deborah D Carr

(57) ABSTRACT

The present invention relates to a method for obtaining a carboxylic acid ester from an aqueous solution of the corresponding carboxylic acid ammonium salt using alcoholysis. The recovered carboxylic acid ester may be subsequently hydrolyzed to produce the corresponding carboxylic acid.

42 Claims, 1 Drawing Sheet

METHOD TO PRODUCE A CARBOXYLIC ACID ESTER FROM A CARBOXYLIC ACID AMMONIUM SALT BY ALCOHOLYSIS

This application claims the benefit of U.S. Provisional Application No. 60/638,126, filed Dec. 22, 2004.

FIELD OF THE INVENTION

The present invention relates to a process of producing a carboxylic acid ester from an aqueous solution of the corresponding carboxylic acid ammonium salt using alcoholysis. The carboxylic acid ester can optionally be hydrolyzed into the corresponding carboxylic acid. Specifically exemplified is a process for preparing methyl glycolate from an aqueous solution of ammonium glycolate using methanolysis. Methyl glycolate obtained by the present process may optionally be hydrolyzed into glycolic acid.

BACKGROUND OF THE INVENTION

Methyl glycolate ($HOCH_2COOCH_3$; CAS Registry Number 96-35-3), has been reported to have a variety of uses similar to that of glycolic acid. Methyl glycolate is used as a solvent for semiconductor processes, as a building block for many cosmetics, and as a cleaner for boilers and metals (Ondrey, G., *Chemical Engineering*, 111(9):20 (2004)). A method to make methyl glycolate from ethylene glycol and methanol has been reported (Ondrey, G., supra). However, this method relies on the use of an expensive gold-based catalyst.

Glycolic acid ($HOCH_2COOH$; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, and as a component in personal care products like skin creams. Glycolic acid also is a principal ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). New technology to commercially produce glycolic acid would be eagerly received by industry.

Enzymatic conversion of glycolonitrile to glycolic acid using an enzyme catalyst (nitrilase or a combination of a nitrile hydratase and an amidase) typically results in the production of an aqueous solution of the ammonium glycolate (U.S. Pat. No. 6,383,786 and U.S. Pat. No. 6,416,980; each herein incorporated by reference). A method to obtain a glycolic acid ester and/or glycolic acid from aqueous solutions comprising ammonium glycolate is needed that separates the desired product easily and efficiently.

One method that has been used to isolate carboxylic acids from the corresponding ammonium salt is reactive solvent extraction. This method has been reported to be useful for extracting lactic acid from ammonium lactate (Wasewar et al., *J. Biotechnol.*, 97:59-68 (2002)). Reactive extraction involves the use of a reactive organic solvent (i.e., an amine) to complex with the acid in the aqueous phase. The first step in the process typically involves acidification of the aqueous solution containing the salt of the desired acid. The acidified aqueous solution is then contacted with an organic solvent typically comprising a reactive amine and one or more diluents. The reactive amine (typically a tertiary alkylamine such as Alamine® 336, Cognis Corp, Cincinnati, Ohio.) reacts with the carboxylic acid forming an acid/amine complex that is soluble in the organic phase. Back extraction is then used to recover the acid from the organic phase. Unfortunately, molar quantities of mineral salts are generated in the process. The economics of using reactive solvent extraction typically requires very efficient organic solvent recycle, as the commercially available tertiary alkyl amines are expensive.

Another method to obtain glycolic acid from ammonium glycolate is thermal decomposition in the presence of an organic solvent optionally including an esterifying agent. The solvent may act by protecting the glycolic acid from reactive ammonia (thereby preventing amide formation) or may act as an organic reactive extraction solvent, thereby aiding in the separation of the acid (Meng et al., US 2004/0210087; hereby incorporated by reference). Optionally, this method can also include an alcohol, thereby creating the ester (which may be more soluble in the organic solvent). The organic solvent may be selected from the group consisting of tertiary alkylamines, alcohols, amides, ethers, ketones, phosphorus esters, phosphine oxides, phosphine sulfides, alkyl sulfides, and combinations thereof. Unfortunately, thermal decomposition in the presence of an organic solvent followed by extraction/back extraction may be problematic as various immiscible fluids form complex physical mixtures that are difficult to separate, a necessary step for effective solvent recycle.

Cockrem (U.S. Pat. No. 6,291,708 B1) teaches rapid heating of a mixture of ammonium salt of an organic acid with alcohol to produce a liquid product stream containing acid, ester, and unreacted ammonium salt. Cockrem fails to address the separation of unreacted salts from the acid and ester.

Filachione et al. (U.S. Pat. No. 2,565,487) teaches a process of producing a carboxylic acid esters from a basic nitrogen salt of an organic carboxylic acid by heating the carboxylic acids in the presence of a refluxing alcohol, typically in the presence of a catalyst such as ammonium sulfate, with an alcohol to produce a complex liquid product mixture comprising the carboxylic acid ester, water, alcohol, and unreacted carboxylic acid salt. The liquid product mixture obtained requires a subsequent distillation step to obtain the carboxylic acid ester.

The problem to be solved is to provide a simple method to obtain a carboxylic acid ester from an aqueous solution comprising the corresponding carboxylic acid ammonium salt.

SUMMARY

The present problem has been solved by providing a method to obtain a carboxylic acid ester from an aqueous solution of the corresponding carboxylic acid ammonium salt in a single step. A heated alcohol vapor feed stream is contacted with an aqueous solution of a carboxylic acid ammonium salt whereby the heated alcohol vapor acts both as 1) an esterifying agent, and 2) a stripping/carrier gas. The resulting carboxylic acid ester is removed from the reaction chamber as a component of the vapor product phase, separating the desired ester product from the aqueous phase within the reaction vessel. The carboxylic acid ester is subsequently recovered (e.g., typically condensed using a direct or indirect contact condenser or a rectifying distillation column) from the vapor product phase. The recovered carboxylic acid ester can be optionally hydrolyzed into the corresponding carboxylic acid. The recovered alcohol may be optionally recycled to the heated alcohol vapor feed stream.

Specifically, a method to produce a carboxylic acid ester from an aqueous solution comprising the corresponding carboxylic acid ammonium salt is provided comprising:

(a) providing
  (i) an aqueous solution comprising a carboxylic acid ammonium salt; said carboxylic acid ammonium salt having the formula:

$R_1-C(O)O^-NH_4^+$ or $NH_4^+{}^-O(O)C-R_1-C(O)O^-NH_4^+$ wherein $R_1$ = C1 to C6 hydrocarbyl group independently selected from the group consisting of alkyl, cycloalkyl, and aryl; optionally substituted with at least one hydroxy group; and
  (ii) a heated alcohol vapor feed stream comprising an alcohol having the formula:

$R_2-OH$ wherein $R_2$ is a C1 to C2 straight chain alkyl group; and
  (iii) a reaction vessel;
(b) contacting said aqueous solution comprising carboxylic acid ammonium salt with said heated alcohol vapor feed stream in said reaction vessel whereby a first vapor product stream is produced comprising a carboxylic acid ester; and
(c) recovering the carboxylic acid ester from said first vapor product stream a) In one embodiment, the process includes a step (d) optionally hydrolyzing the carboxylic acid ester of step (c) into the corresponding carboxylic acid.

The carboxylic acid product step (d) may be recovered.

In a preferred embodiment, a method to produce glycolic acid ester from an aqueous solution of ammonium glycolate is provided comprising:

(a) providing
  (i) an aqueous solution comprising ammonium glycolate; and
  (ii) a heated alcohol vapor feed stream comprising an alcohol having the formula:

$R_2-OH$ wherein $R_2$ is a C1 to C4 straight chain or branched alkyl group; and
  (iii) a reaction vessel;
(b) contacting said aqueous solution comprising ammonium glycolate with said heated alcohol vapor feed stream in said reaction vessel whereby a first vapor product stream is produced comprising a glycolic acid ester; and
(c) recovering the glycolic acid ester from said first vapor product stream.

In one embodiment, the process includes a step (d) optionally hydrolyzing the glycolic acid ester of step (c) into glycolic acid. The glycolic acid product of step (d) may be recovered.

In one preferred embodiment, the heated alcohol vapor feed stream is a heated methanol vapor feed stream and the carboxylic acid ammonium salt is ammonium glycolate.

BRIEF DESCRIPTION OF THE FIGURE

The invention can be more fully understood from the FIGURE and the detailed description that together form this application.

Figure 1:
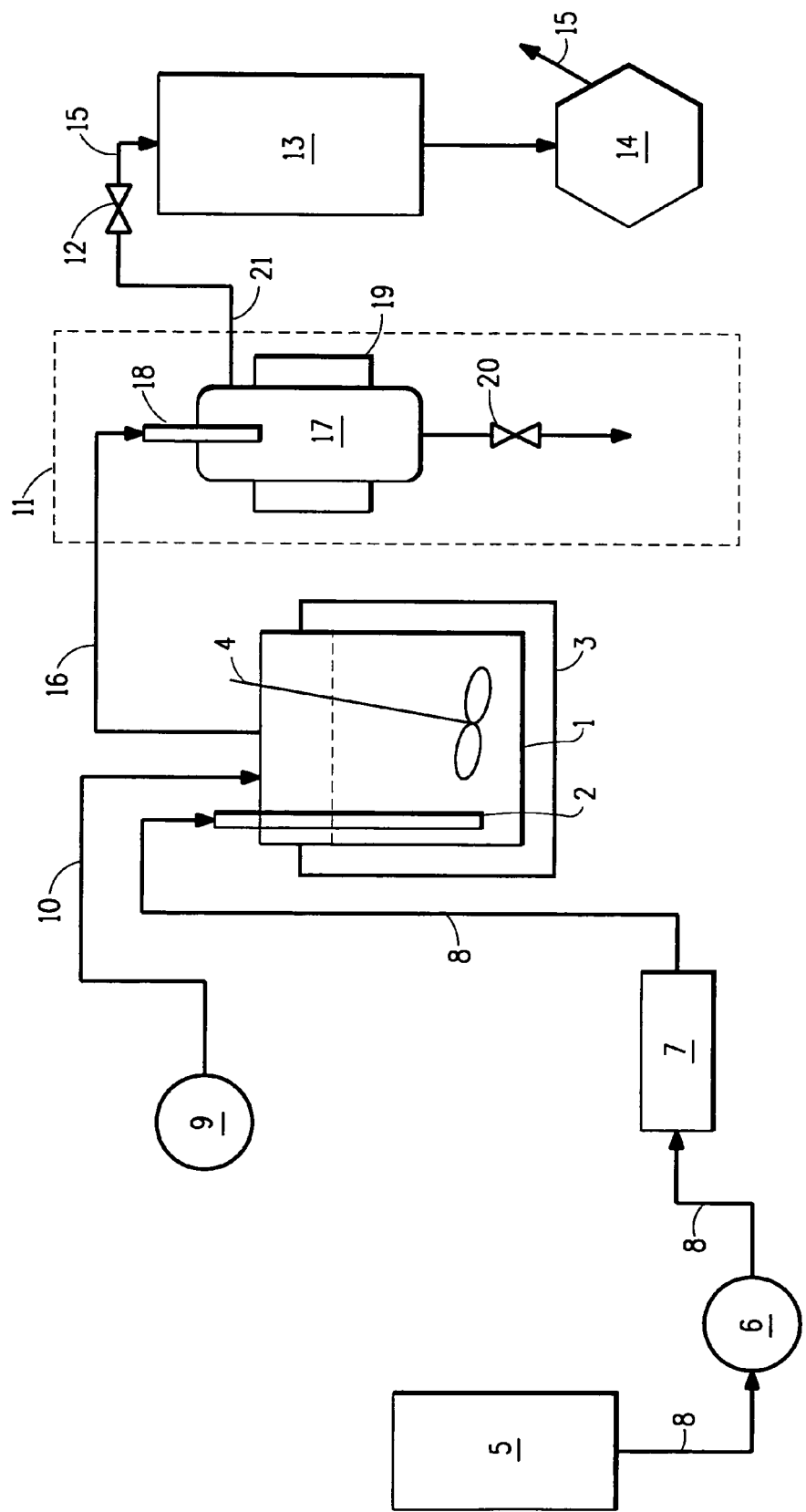
FIG. 1 shows the general design of one laboratory method and system used to obtain a carboxylic acid ester from an aqueous solution of the corresponding carboxylic acid ammonium salt. A 300 cc HASTELLOY® C autoclave (Autoclave Engineers; Snap-tite Corp., Erie, Pa.) suitable for 5000 psig (~34,474 kPa) pressure operation (1) containing a dip leg (2), an electrical heating system (3), and a magna drive air driven agitator (4) is connected to two feed systems and one vapor recovery system.

The first feed system for alcohol is composed of a 1000-mL graduated cylinder (5), a Beckman Model #114M pump (6), a two stage heater (7) with a steam heated first stage and electric heated second stage, and $\frac{1}{8}^{th}$ (3.18 mm) inch stainless steel tubing (8) and valves to connect the equipment together and to the dip tube in the autoclave.

The second feed system for the reactant is composed of a 500 cc Isco syringe pump Model 500D with stainless steel internal components (9) and $\frac{1}{8}^{th}$ inch (3.18 mm) stainless steel tubing (8) and valves to connect the pump to the top of the autoclave (10).

The vapor recovery system consists of a hot condenser (11), a stainless steel Grove dome loaded back pressure regulator (12), a cold water cooled coaxial condenser coil (13) with $\frac{3}{8}$ inch (9.53 mm) stainless steel internal tube and 1 inch (25.4 mm) outside stainless steel tube, a 5 gallon (18.93 Liters) stainless steel collection drum (14) and a vent line (15) with ¼ inch (6.53 mm) stainless steel tubing (16) connecting the components. The hot condenser (11) is constructed from a 500 cc Hoke cylinder (17) (Hoke, Inc., Spartanburg, S.C.) modified with a dip tube (18) that directs the vapor ½ down the length of the cylinder, external coils (19) containing steam to cool the vapors, a sample line and valve (20) at the bottom of the cylinder to periodically recover samples and a vapor exit (21).

DETAILED DESCRIPTION OF THE INVENTION

The stated problem has been solved by providing a method to obtain a carboxylic acid ester from an aqueous solution of the corresponding carboxylic acid ammonium salt using alcoholysis. The carboxylic acid ester obtained by the present process may be subsequently hydrolyzed to produce the corresponding carboxylic acid and the corresponding alcohol. The alcohol may be subsequently recycled for use in the heated alcohol vapor feed stream.

A method is provided wherein a heated alcohol vapor feed stream is used to convert a carboxylic acid ammonium salt into the corresponding ester (Equation 1). The carboxylic acid may be a mono- or dicarboxylic acid ammonium salt.

$$R_1C(O)O^-NH_4^+ + R_2OH \rightarrow R_1C(O)OR_2 + NH_3 + H_2O$$

or $$NH_4^+{}^-O(O)CR_1C(O)O^-NH_4^+ + 2(R_2OH) \rightarrow R_2O(O)CR_1C(O)OR_2 + 2NH_3 + 2H_2O \quad \text{Equation 1.}$$

In a preferred embodiment, the carboxylic acid ammonium salt is ammonium glycolate as shown in Equation 2.

$$HOCH_2CO_2^-NH_4^+ + R_2OH \rightarrow HOCH_2CO_2R_2 + NH_3 + H_2O \quad \text{Equation 2.}$$

The glycolic acid ester is carried as a vapor product from the reactor and is recovered from the vapor product stream using a method including, but not limited to adsorption, simple condensation, membrane separation, or distillation. Optionally, the recovered glycolic acid ester can be subsequently hydrolyzed to glycolic acid.

Suitable alcohols useful in the present invention are typically monohydroxy alcohols. In one aspect, the alcohol is an alkyl alcohol represented by the following formula:

$$R_2\text{—OH}$$

where $R_2$ is a C1 to C4 straight chain or branched chain alkyl group. In a preferred aspect, $R_2$ is a C1 to C2 alkyl group. In another preferred aspect, the alkyl alcohol is selected from the group consisting of methanol, ethanol, n-propanol, isopropanol, n-butanol, isobutyl alcohol, and t-butanol. In yet a more preferred aspect, the alcohol is selected from the group consisting of methanol and ethanol. In yet an even more preferred embodiment, the alcohol is methanol (i.e, forms carboxylic acid methyl esters such as methyl glycolate).

The present method provides a method to produce carboxylic acid ester (e.g, methyl glycolate) and/or carboxylic acid (e.g., glycolic acid) from an aqueous solution of the corresponding carboxylic acid ammonium salt (e.g., ammonium glycolate). The esterifying agent (i.e., heated alcohol vapor) is selected so that the resulting carboxylic acid ester is a vapor in the vapor product stream. The carboxylic acid ester is subsequently recovered as a liquid from the vapor product stream. In an optional embodiment, the recovered carboxylic acid ester is subsequently hydrolyzed into the corresponding carboxylic acid.

Definitions:

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the term "hydrocarbyl" refers to aliphatic, cycloaliphatic or aromatic groups comprising carbon and hydrogen. Hydrocarbyl is understood to include cyclic, branched or linear substituted hydrocarbyl groups with the latter referring to the hydrocarbon portion bearing additional substituents such as hydroxyl groups. Examples of hydrocarbyl groups include, but are not limited to methyl, ethyl, propyl, isopropyl, butyl, isobutyl, t-butyl, cyclopropyl, cyclobutyl, pentyl, cyclopentyl, hexyl, cyclohexyl, benzyl, and phenyl groups. In one embodiment, the hydrocarbyl group is selected from the group consisting of methyl, ethyl, n-propyl, n-butyl, n-pentyl, and n-hexyl groups optionally substituted with at least one hydroxy group. In another embodiment, the hydrocarbyl group is a hydroxy-substituted hydrocarbyl group selected from the group consisting of hydroxymethyl, hydroxyethyl, and hydroxybutyl. In yet another embodiment, the hydroxy-substituted hydrocarbyl group is hydroxymethyl.

As used herein, the term "substituted" means a group that is substituted and contains one or more substituent groups that do not cause the compound to be unstable or unsuitable for the use or reaction intended. In one embodiment, the substituent group is a hydroxy group. In another embodiment, the hydroxy group is substituted on the α-carbon adjacent to a carboxyl group (e.g., an α-hydroxyacid).

As used herein, the term "carboxylic acid ammonium salt" will be used to refer to the mono- or diammonium salts of a mono- or dicarboxylic acids, respectively, having the following formula:

$$R_1C(O)O^-NH_4^+ \text{ or } NH_4^+{}^-O(O)CR_1C(O)O^-NH_4^+$$

wherein $R_1$ is a C1 to C6 hydrocarbyl group independently selected from the group consisting of alkyl, cycloalkyl, and aryl; said hydrocarbyl group optionally substituted with at least one hydroxyl group. In one embodiment, the carboxylic acid ammonium salt is selected from the group consisting of ammonium acetate, ammonium propionate, ammonium butyrate, ammonium pentanoate, ammonium hexanoate, ammonium glycolate, ammonium lactate, diammonium adipate, diammonium succinate, diammonium glutarate, diammonium terephthalate, diammonium phthalate, and diammonium isophthalate. In another embodiment, the carboxylic acid ammonium salt is a 2-hydroxycarboxylic acid ammonium salt. In yet another embodiment, the 2-hydroxycarboxylic acid ammonium salt is selected from the group consisting of ammonium lactate and ammonium glycolate. In yet another embodiment, the 2-hydroxyacid ammonium salt is ammonium glycolate.

As used herein, the term "carboxylic acid ester" will be used to refer to the mono- or diesters of carboxylic acids, respectively, having the following formula:

$$R_1C(O)OR_2 \text{ or } R_2O(O)CR_1C(O)OR_2$$

wherein $R_1$ is a C1 to C6 hydrocarbyl group independently selected from the group consisting of alkyl, cycloalkyl, and aryl; said hydrocarbyl group optionally substituted with at least one hydroxyl group and $R_2$ is a C1 to C4 (1 to 4 carbon atoms) straight chain or branched chain alkyl groups. In a preferred embodiment, $R_2$ is a ethanol or methanol. In another embodiment, the carboxylic acid ester is selected from group consisting of acetic acid ester, propionic acid ester, butyric acid ester, pentanoic acid ester, hexanoic acid ester, glycolic acid ester, lactic acid ester, adipate acid diester, succinate acid diester, glutaric acid diester, terephthalic acid diester, phthalic acid diester, and isophthalic acid diester. In another embodiment, the carboxylic acid ester is selected from group consisting of methyl acetate, methyl propionate, methyl butyrate, methyl pentanoate, methyl hexanoate, methyl glycolate, methyl lactate, dimethyl adipate, dimethyl succinate, dimethyl glutarate, dimethyl terephthalate, dimethyl phthalate, and dimethyl isophthalate. In yet another embodiment, the carboxylic acid ester is a 2-hydroxycarboxylic acid ester. In still yet another embodiment, the 2-hydroxycarboxylic acid ester is selected from the group consisting of lactic acid ester and glycolic acid ester. In a further embodiment, the 2-hydroxycarboxylic acid ester is glycolic acid ester. In still a further embodiment, the 2-hydroxycarboxylic acid ester is methyl glycolate.

As used herein, the term "carboxylic acid" will be used to refer carboxylic acids having the following formula:

$$R_1C(O)OH \text{ or } HO(O)CR_1C(O)OH$$

wherein $R_1$ is a C1 to C6 hydrocarbyl group independently selected from the group consisting of alkyl, cycloalkyl, and aryl; said hydrocarbyl group optionally substituted with at least one hydroxyl group. In one embodiment, the carboxylic acid is selected from group consisting of acetic acid, propionic acid, butyric acid, pentanoic acid, hexanoic acid, glycolic acid, lactic acid, adipic acid, succinic acid, glutaric acid, terephthalic acid, phthalic acid, and isophthalic acid. In another embodiment, the carboxylic acid is a 2-hydroxycarboxylic acid. In yet another embodiment, the 2-hydroxycarboxylic acid is selected from the group consisting of lactic acid and glycolic acid. In a further embodiment, the 2-hydroxycarboxylic acid is glycolic acid.

As used herein, the term "glycolonitrile" is abbreviated as "GLN" and is synonymous with hydroxyacetonitrile, 2-hydroxyacetonitrile, hydroxymethyinitrile, and all other synonyms of CAS Registry Number 107-16-4.

As used herein, the term "glycolic acid" is abbreviated as "GLA" and is synonymous with hydroxyacetic acid, hydroxyethanoic acid, and all other synonyms of CAS Registry Number 79-14-1.

As used herein, the term "ammonium" refers to the cation having the formula $NH_4^+$.

As used herein, the term "ammonium glycolate" is the ammonium salt of glycolic acid and is abbreviated as "$NH_4GLA$".

The term "ammonia" will be used to refer to the compound having CAS Registry Number 7664-41-7 and is represented by the formula $NH_3$.

As used herein, the term "methyl glycolate" is the methyl ester of glycolic acid and is abbreviated as "MeGLA" and is synonymous with methyl 2-hydroxyacetate and all other synonyms of CAS Registry Number 96-35-3.

As used herein, the term "carboxylic acid methyl ester" refers to the methyl ester of a carboxylic acid.

As used herein, the term "alcoholysis" refers to the process of reacting an aqueous solution of a carboxylic acid ammonium salt with a heated alcohol vapor that acts as both an esterifying agent and stripping gas (FIG. 1), producing a vapor product stream comprising the carboxylic acid ester. As used herein, the term "methanolysis" refers to the process of alcoholysis wherein the alcohol is methanol.

As used herein, the term "esterification agent" or "esterifying agent" will refer to the heated alcohol vapors used in the present invention.

As used herein, the terms "C1 to C4 alcohol" refer to straight chain or branched alkyl alcohols having the formula:

$R_2$—OH wherein $R_2$ is a C1 to C4 (1 to 4 carbon atoms) straight chain or branched chain alkyl groups. In one embodiment, the C1 to C4 alcohol is an alcohol selected from the group consisting of methanol, ethanol, n-propanol, isopropanol, n-butanol, isobutyl alcohol, and t-butanol. In another embodiment, the alcohol is selected from the group consisting of methanol, ethanol, and n-propanol. In a preferred embodiment, $R_2$ is a C1 to C2 alkyl group (i.e., ethanol or methanol). In one preferred embodiment, the alcohol is a methanol.

As used herein, the terms "heated alcohol vapor" and "alcohol vapor feed stream" refer to the heated alcohol vapor that in the present process is contacted with the aqueous solution of the carboxylic acid ammonium salt whereby a carboxylic acid ester is produced; wherein the carboxylic acid ester product is in the vapor phase. An excess amount of heated alcohol vapor is reacted with ammonium salt of the carboxylic acid whereby the heated alcohol vapor carries the carboxylic acid ester in the vapor product stream (first vapor product stream). In one embodiment, the heated alcohol vapor is a C1 to C4 alcohol that is heated to a temperature of at least about 70° C. above the normal boiling point of the alcohol (as measured at 1 atmosphere). Table 1 shows the respective boiling points for several C1 to C4 alcohols.

TABLE 1

Examples C1 to C4 alcohols and their Normal Boiling Points (NBPs)

| Name | Formula | Boiling point (° C.) at 1 atm. (~101.33 kPa) |
|---|---|---|
| Methanol | $CH_3OH$ | ~64.7 |
| Ethanol | $CH_3CH_2OH$ | ~78.3 |
| Propanol | $CH_3CH_2CH_2OH$ | ~97.2 |
| Isopropanol | $CH_3CH(OH)CH_3$ | ~82.3 |
| Butanol | $CH_3CH_2CH_2CH_2OH$ | ~117.7 |
| Isobutyl alcohol | $CH_3CH(CH_3)CH_2OH$ | ~108 |
| sec-Butanol | $CH_3CH_2CH(OH)CH_3$ | ~99.5 |
| tert-Butanol | $(CH_3)_3COH$ | ~82.5 |

Selecting the appropriate operating temperature and pressure for the reaction (i.e, reaction vessel temperature and pressure) must consider the vapor pressure of both the alcohol and the corresponding carboxylic acid ester. At the selected operating pressure, the reaction temperature is selected so that the vapor pressure of the carboxylic acid ester is typically at least about one quarter (¼) of the operating pressure of the system. At this temperature the vapor pressure of the alcohol should exert at least about 4 times (4×) the operating pressure.

The temperature of the heated alcohol vapor feed stream entering the reaction chamber may vary according to the selected alcohol as well as the specific equipment geometry. The heated alcohol vapor fed acts as a source of heat for the reaction, an esterifying agent, and as a stripping/carrying gas for the carboxylic acid ester formed by the present process. To illustrate this point consider the laboratory equipment in FIG. 1 operating with methanol as the alcohol and methyl glycolate as the ester product.

Typically, the temperature of the heated methanol vapor is about 140° to about 350° C. In one embodiment, the temperature of the methanol vapor feed stream is about 170° C. to about 300° C. In another embodiment, the temperature of the methanol vapor feed stream is about 230° C. to about 250° C.

The carboxylic acid ester (vapor) formed by the present alcoholysis process can be subsequently recovered/isolated from the first vapor product stream using methods known in the art. Methods to recover/isolate the carboxylic acid ester from the first vapor product stream are well known in the art and include, but are not limited to membrane separation, adsorption, direct or indirect contact condensation (e.g., partial condenser), use of distillation column(s), and combinations thereof.

One of skill in the art can adjust the flow rate and temperature of the heated alcohol vapor feed stream to optimize the amount of carboxylic acid ester in the resulting first vapor product stream. The majority of the undesirable impurities (i.e. unreacted carboxylic acid ammonium salts, mineral salts, etc.) remain in the reaction vessel in the liquid phase.

As used herein, the terms "first vapor product stream", "vapor product stream", and "alcohol vapor product stream" refer to the vapor product stream comprising the heated alcohol vapor and the carboxylic acid ester (vapor) produced by alcoholysis. The carboxylic acid ester can be recovered from the vapor product stream by methods known in the art including, but not limited to adsorption, membrane systems, condensation (e.g., a partial condenser), use of distillation column (s), and combinations thereof. The recovered carboxylic acid ester (liquid) is collected in the "first liquid product stream". As used herein, the term "first liquid product stream" refers to the liquid product comprising the carboxylic acid ester recovered from the first vapor product stream. In one embodiment, a partial condenser is used to recover the carboxylic acid ester from the first vapor product stream where the most of the heated alcohol vapor passes through the partial condenser ("hot condenser") and is subsequently recovered using a total condenser ("cold condenser"). The recovered alcohol may be recycled and reused at the starting material for the heated vapor feed stream. Any ammonia or water recovered may be optionally removed from the recovered alcohol prior to being recycled.

As used herein, the terms "aqueous solution feed stream", "aqueous feed stream", "aqueous solution comprising carboxylic acid ammonium salt", and "carboxylic acid ammonium salt feed stream" are used interchangeably to describe the aqueous solution comprising carboxylic acid ammonium salt. The aqueous feed stream may be pre-charged in the reaction vessel or may be metered into the reaction vessel prior to being contacted with the heated alcohol vapor feed stream. The aqueous feed stream is typically comprised of the carboxylic acid ammonium salt targeted for conversion into the corresponding carboxylic acid ester. The aqueous feed stream may also be comprised of the corresponding carboxylic acid depending on the pH of the aqueous feed stream and the pKa of the corresponding acid. In a preferred embodiment, the pH of the aqueous feed stream is maintained above the pKa of the corresponding carboxylic acid. In an alternative embodiment, the pH may be adjusted. In a preferred embodiment, the aqueous feed stream is primarily comprised of the carboxylic acid ammonium salt (i.e., pH of aqueous feed stream above the pKa of the corresponding carboxylic acid). In yet another preferred embodiment, the aqueous feed stream comprises ammonium glycolate.

The aqueous solution feed stream may comprise a fermentation broth that is unpurified or at least partially purified. The fermentation broth may also be comprised of other organic salts, inorganic salts, protein fragments, sugar residues, other organic acids, alcohols, ketones, and metal ions. The fermentation broth can be partially purified by filtration or centrifugation to remove excess debris. Furthermore, the aqueous solution feed stream can be partially purified using one or more other ways known in the art. In one embodiment, the feed stream may also be concentrated prior to being used as a feed stream in the present invention.

The aqueous feed stream is comprised of the carboxylic acid ammonium salt at a concentration of at least about 0.1 weight percent (wt %) to about 99 wt %. In another embodiment, the aqueous feed stream is comprised of at least about 10 wt % to about 75 wt % carboxylic acid ammonium salt. In a further embodiment, the aqueous reaction mixture is comprised of at least about 20 wt % to about 50 wt % carboxylic acid ammonium salt. In a preferred embodiment, the aqueous feed stream comprises at least about 0.1 wt % to about 99 wt %, preferably about 10 wt % to about 75 wt %, and most preferably about 20 wt % to about 50 wt % ammonium glycolate.

The pH of the aqueous reaction mixture can be about 4 to about 12, preferably about 5 to about 10, more preferably about 6 to about 8. The pH can be adjusted as needed prior to use as a starting material in the present method.

Suitable Conditions for Alcoholysis

A process/method to obtain a carboxylic acid ester from an aqueous solution of carboxylic acid ammonium salt (mono- or diammonium salt) in a single step is provided herein. A heated alcohol vapor is contacted with an aqueous solution comprising at least one carboxylic acid ammonium salt ("aqueous feed stream"). The alcohol reacts with the carboxylic acid ammonium salt, forming the corresponding carboxylic acid ester as show in Equation 1.

The amount of heated alcohol vapor contacted with the carboxylic acid ammonium salt is typically in a molar excess relative to the amount of carboxylic acid ammonium salt in the aqueous feed stream. The molar ratio of the heated alcohol vapor to the carboxylic acid ammonium salt may vary, but it typically from about 5 to about 300 moles per mole of carboxylic acid ammonium salt (molar ration at least about 5:1 to about 300:1), preferably about 5 to about 200 moles per mole of the carboxylic acid ammonium salt, most preferably about 20 to about 100 moles per mole of carboxylic acid ammonium salt. A molar excess of the alcohol vapor tends to inhibit amide formation.

The alcohol vapor feed stream (e.g., methanol) temperature is typically chosen to ensure that the alcohol generally remains in its vapor phase so that it acts as both an esterifying agent and a stripping/carrying gas. The temperature of the heated alcohol vapor feed stream entering the reaction chamber may vary according to the selected alcohol and the resulting carboxylic acid ester as well as the specific equipment geometry. The heated alcohol vapor fed acts as a source of heat for the reaction, an esterifying agent, and as a stripping/carrying gas for the carboxylic acid ester formed by the present process. To illustrate this point consider the laboratory equipment in FIG. 1 operating with methanol as the alcohol and methyl glycolate as the ester product.

Typically, the temperature of the heated methanol vapor is about 140° to about 350° C. In one embodiment, the temperature of the methanol vapor feed stream is about 170° C. to about 300° C. In another embodiment, the temperature of the methanol vapor feed stream is about 230° C. to about 250° C.

The reactor pressure and temperature can be adjusted to optimize production of the desired product. Selecting the appropriate operating temperature and pressure for the reaction must consider the vapor pressure of both the alcohol and the corresponding carboxylic acid ester. At the selected operating pressure, the reaction temperature is selected so that the vapor pressure of the carboxylic acid ester is typically at least about one quarter (¼) of the operating pressure of the system. At this temperature the vapor pressure of the alcohol should exert at least about 4 times (4×) the operating pressure. A typical operating pressure is from about 0 psig (~0 kilopascals (kPa)) to about 80 psig (~550 kPa), preferably about 0 psig (0 kPa) to about 50 psig (345 kPa), and most preferably about 10 psig (69 kPa) to about 50 psig (345 kPa).

A typical operating temperature for the reactor is about 140° C. to about 300° C., preferably about 170° C. to about 200° C. In one aspect, the carboxylic acid ammonium salt is ammonium glycolate and the alcohol is methanol. The reactor temperature used this particular combination is typically about 100° C. to about 300° C., preferably about 150° C. to about 250° C., more preferably about 170° C. to about 225° C., and most preferably about 170° C. to about 200° C.

The reactor may optionally include a packing material or a high boiling point fluid/liquid to improve the yield of the desired carboxylic acid ester. The benefit of the packing or high boiling point fluid is to improve the contacting between the aqueous salt solution and the alcohol vapor. The packing may be random packing, engineered packing, or various distillation plate designs. See Perry's 7$^{th}$ edition Chapter 14.23 through 14.61 (*Perry's Chemical Engineers' Handbook, 7$^{th}$ ed.*, Perry, Robert H., Green, Dow W., and Maloney, James O., editors; McGraw Hill Companies, Inc., New York, N.Y., 1997). Commercial designs for gas liquid reaction systems are illustrated in Perry's FIGS. 23-25, 23-26, and 13-79. The high boiling point fluid should be selected to have a low vapor pressure at the chosen operating conditions or be easily separated from the recovered ester. The high boiling point fluid may be inert to the esterification chemistry (such as mineral oil) or potentially participate in the esterification chemistry such as a polyol. The polyol is a material with a molecular weight greater than 150 and at least one hydroxyl group, including monohydroxy alcohols such as decanol and dodecanol. Typical polyols include larger alcohols such as decanol and dodecanol as well as large diols such as polyethylene ether glycol (PEG), polypropylene ether glycol (PPG), polytetramethylene ether glycol (PTMEG), as well as copolymers of these polyalkylene ether glycols, and mixtures thereof.

Recovering the ester as a liquid from the first vapor product may be accomplished by reducing the temperature of the vapor to form a condensate. The cooling may be accomplished in a direct or indirect contact condenser (see Perry's Chapter 11; supra). In way of illustration, for laboratory equipment in FIG. 1 operating with methanol as the alcohol and methyl glycolate as the ester operating at 25 psig, the indirect contact condenser ("hot condenser") temperature is typically maintained at or below the boiling point of the respective carboxylic acid ester but above the normal boiling point of the heated alcohol vapor. Typically, the partial condenser temperature is maintained at least about 10° C. to about 100° C. below the normal boiling point of the ester. Control of the alcohol vapor temperature, the reactor pressure, and the partial condenser temperatures should be used to selectively condense the desired carboxylic acid ester from the corresponding esterifying agent (i.e. the alcohol), water, and ammonia vapors.

Distillation may also be used to obtain the carboxylic acid ester from the vapor product stream. Distillation designs (e.g., generally comprised of a reflux column, an overhead condenser, and reflux control) are well know. Commercial designs for distillation systems may be found in Perry's Chapter 13. Designs with multiple product removal may be particularly well suited for recovering the ester (See Perry's FIG. 13-6.).

It is contemplated that the gas liquid contacting operation and the ester recovery from the first vapor product operation may be accomplished in a single device.

The corresponding carboxylic acid can subsequently be obtained by simply hydrolyzing the carboxylic acid ester collected in the first liquid product stream (i.e., from the partial condenser). Techniques to hydrolyze esters to acids are known to those skilled in the art. The recovered ester can be combined with water and placed into a short path batch distillation apparatus containing a short fractionating column and a total condenser. Heating the mixture will drive methanol overhead as well as some of the water, leaving the carboxylic acid behind in the heated mixture.

Producing Methyl Glycolate and/or Glycolic Acid from Ammonium Glycolate

The present method is exemplified by producing methyl glycolate from an aqueous solution of ammonium glycolate using heated methanol vapor feed stream. A general alcoholysis (e.g., methanolysis) system is shown in FIG. 1.

An aqueous ammonium glycolate solution was fed into a reactor (e.g. autoclave) using a feed pump. Methanol was pumped from a methanol feed tank through a series of heaters (i.e., steam heater(s) and electric coil heater(s)), forming a heated alcohol vapor feed stream. The pressure in the system was maintained at about 25 psig.

The product (methyl glycolate vapor), methanol, water, and ammonia exited as vapor on top ("first vapor product stream"). Unreacted feed material and byproducts were mostly retained in the bottom of the reaction vessel as a liquid/solid purge. The vapor exiting the top of the reactor was transferred to a partial condenser, where the methyl glycolate vapor was condensed and recovered in the first liquid product stream. A pressure control valve was used to adjust the pressure in the system. A methanol pump can be used to optionally feed the recovered methanol back into the heated alcohol vapor feed stream.

Optionally, the glycolic acid ester in the first liquid product stream can be recovered using a variety of techniques such as distillation. The glycolic acid ester can be converted into glycolic acid and the corresponding alcohol by hydrolysis of the ester bond. The hydrolysis can be accomplished chemically or enzymatically (i.e., use of an esterase, protease, etc.). Method to hydrolyze carboxylic acid esters are well-known in the art (see Gurthrie, J. and Cullimore, P., Can J. Chem., 58(13):1281-1294 and US2004/0138409 A1 [in particular, page 23, column 1], herein incorporated by reference).

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

GENERAL METHODS

The abbreviations in the specification correspond to units of measure, techniques, properties, or compounds as follows: "sec" or "s" means second(s), "min" means minute(s), "h" or "hr" means hour(s) "µM" means micromolar, "mM" means millimolar, "M" means molar, "wt" means weight, "wt %" means weight percent, "g" means grams, "L" means liters, "mL" means milliliters, "cc" means cubic centimeters, "kPa" means kilopascals, "$^1$H NMR" means proton nuclear magnetic resonance spectroscopy, "rpm" means revolutions per minute, "GLA" means glycolic acid, "NH$_4$GLA" means ammonium glycolate, "MeGLA" means methyl glycolate, and "MeOH" means methanol.

$^1$H NMR Analytical Method

An aliquot of sample (0.40 mL) was mixed with an equal volume of CDCl$_3$ containing 0.1% TMS (tetramethylsilane), and the resulting solution analyzed by $^1$H NMR spectroscopy (500 MHz) and $^{13}$C NMR spectroscopy (125 MHz). Samples were found to contain methanol, methyl glycolate, ammonium glycolate and glycolic acid, and the $^1$H NMR chemical shifts relative to TMS for the respective methylene and/or methoxy hydrogen atoms of these compounds are listed in Table 2 (when no ammonium is present in the sample) and Table 3 (when ammonium is present in the sample).

TABLE 2

| Compound | Reference Peaks | Reference Peak |
|---|---|---|
| $CH_3OH$ | $C\underline{H}_3O$—, singlet, $\delta = 3.388$ | |
| $HOCH_2C(O)OCH_3$ | $HOC\underline{H}_2$—, singlet, $\delta = 4.176$ | —$OC\underline{H}_3$, singlet, $\delta = 3.758$ |
| $HOCH_2C(O)OH$ | $HOC\underline{H}_2$—, singlet, $\delta = 4.153$ | |

When ammonium is present in the sample the glycolic acid peak shifts as follows:

TABLE 3

| Compound | Reference Peaks | Reference Peak |
|---|---|---|
| $CH_3OH$ | $C\underline{H}_3O$—, singlet, $\delta = 3.388$ | |
| $HOCH_2C(O)OCH_3$ | $HOC\underline{H}_2$—, singlet, $\delta = 4.176$ | —$OC\underline{H}_3$, singlet, $\delta = 3.758$ |
| $HOCH_2C(O)OH$ | $HOC\underline{H}_2$—, singlet, $\delta = 4.016$ | |
| $HOCH_2C(O)ONH_4$ | $HOC\underline{H}_2$—, singlet, $\delta = 3.945$ | |

The identity of the compounds identified in the table above were confirmed by individually adding methanol, methyl glycolate, ammonium glycolate, or glycolic acid to a second aliquot of a reference sample and observing an increase in the relative peak integration for the respective methylene and/or methoxy hydrogen atoms of these compounds. The molar ratio of the components of each sample were determined by integration of the portion of the $^1H$ NMR spectra containing the respective methylene or methoxy H-atoms of the chemical components.

EXAMPLE 1

Conversion of Glycolic Acid to Methyl Glycolate Using Heated Methanol Vapor as Esterifying Agent and Stripping Gas The purpose of Example 1 is to illustrate the ability of the present process to convert an aqueous solution of glycolic acid into methyl glycolate using heated methanol vapor as an esterifying agent and stripping gas. The methyl glycolate product was removed from the reaction chamber and selectively isolated from the vapor product stream using a partial condenser.

The general design of the process is shown in FIG. 1. Approximately 137 g of polytetramethylene ether glycol (PT-MEG, used as a high boiling point fluid; Lyondell PolyMeg® 1000, product number 9707; Lot #PEZM30B-A; Lyondell Chemical Company, Houston, Tex.; CAS#25190-06-1) was charged to the reaction chamber (300 cc autoclave). The pressure controller (loaded back pressure regulator) was adjusted to 25 psig (~172.4 kPa). The autoclave agitator was started and set at 1000 rpm. The autoclave internal temperature was set at 200° C. and the hot condenser surface temperature was set at 130° C. Once temperatures equilibrated, methanol (Brenntag Northeast Inc., Reading, Pa.; 99.99% pure, product code 838775) flow was initiated at 10 mL/min and methanol feed temperature to the autoclave was maintained at 250° C. The conditions were maintained for 45 minutes to allow the system to come to equilibrium. Glycolic acid feed (70 wt % aqueous solution; Sigma-Aldrich, Catalog # 420581) was then initiates at 1.5 mL/min and maintained for 45 minutes for a total feed of 67 mL. Methanol flow was continued an additional 20 minutes past termination of the ammonium glycolate flow. Total methanol feed was 1160 mL.

Samples were collected from the hot condenser every 5 minutes during the methanol feed. The samples were analyzed by proton nuclear magnetic resonance spectroscopy ($^1H$ NMR) and found to contain methanol, methyl glycolate, and glycolic acid. Results for samples from the hot condenser (2-3, 2-5, and 2-7) and the stainless steel collection drum (2-drum) are presented in Table 4. The molar ratio was reported by standardizing the methyl glycolate peak (i.e. the "$CH_3$ peak") area to 1.

TABLE 4

Molar ratio of methanol, methyl glycolate, and glycolic acid in samples from the hot condenser or stainless steel collection drum. Molar ratio calculated by standardizing methyl glycolate peak area to 1.

| Collection time (minutes) | Sample Identification No. | Methanol (MeOH) | Methyl Glycolate (MeGLA) | Glycolic Acid (GLA) |
|---|---|---|---|---|
| 10-15 | 2-3 | 3.8 | 1.0 | 0.1 |
| 20-25 | 2-5 | 3.2 | 1.0 | 0.2 |
| 30-35 | 2-7 | 2.9 | 1.0 | 0.2 |
| | 2-drum | 199.5 | 1.0 | nd | nd—not detectable

The system was cooled down and samples were recovered from various vessels and a material balance was performed. Total mass balanced within 99%. The reactor contained 138 g of viscous liquid. The methanol recovery drum contained 912 g. and the total weight of all samples was 99 grams.

EXAMPLE 2

Conversion of Ammonium Glycolate to Methyl Glycolate Using Heated Methanol Vapor as Esterifying Agent and Stripping Gas (Reactor Temperature~200° C.; Hot Condenser~130° C.)

The purpose of Example 2 is to show the direct conversion of an aqueous solution of ammonium glycolate to methyl glycolate using heated methanol vapor as an esterifying agent and stripping gas. The general process design is shown in FIG. 1.

An aqueous ammonium glycolate ($NH_4GLA$) solution (ammonium glycolate "solution A") was prepared by combining 659 g of 70 wt % aqueous glycolic acid solution (Sigma-Aldrich) with 357 g of 30 wt % aqueous ammonium hydroxide solution (EMD Chemicals, Darmstadt, Germany; product no. AX1303-6).

Approximately 138 g of PTMEG was charged to the reactor (autoclave). The pressure controller was adjusted to 25 psig (~172.4 kPa). The autoclave agitator was started and set at 1000 rpm. The autoclave temperature was set at 200° C. and the hot condenser was set at 130° C. Once temperatures equilibrated, methanol flow was initiated at 10 mL/min and methanol feed temperature to the autoclave was maintained at 250° C. The conditions were maintained for 15 minutes to allow the system to come to equilibrium. Ammonium Glycolate solution A was then pumped to the reactor at a rate of 2.2 mL/min and maintained for 60 minutes for a total feed of 132 mL. Methanol flow was continued an additional 35 minutes past termination of the ammonium glycolate feed. Total methanol feed was 1110 mL.

Samples were collected from the hot condenser (FIG. 1, #17) every 5 minutes during the ammonium glycolate feed. The first 30 minutes of samples were combined to make samples designated with an "A" and the second 30 minutes of samples were combined to make samples designated with a "B". The samples (samples "5A" and "5B") were analyzed by $^1$H NMR and found to contain methanol, methyl glycolate, and ammonium glycolate. Results are summarized in Table 4.

The system was cooled down and samples were recovered from various vessels and a material balance was performed. The autoclave contained 140 g of viscous liquid. The methanol recovery drum contained 913 g and the total weight of all samples was 123 grams.

EXAMPLE 3

Conversion of Ammonium Glycolate to Methyl Glycolate Using Heated Methanol Vapor as Esterifying Agent and Stripping Gas (Reactor Temperature~170° C.; Hot Condenser~100° C.)

Equipment and procedures were identical to Example 2 except the reactor (autoclave) temperature was maintained at 170° C. and the hot condenser was maintained at 100° C. Ammonium glycolate solution A was fed for 60 minutes and samples were combined as described in Example 1 to prepare samples "7A" and "7B". Results are summarized in Table 5.

EXAMPLE 4

Conversion of Ammonium Glycolate to Methyl Glycolate Using Heated Methanol Vapor as Esterifying Agent and Stripping Gas (Mineral Oil as Heat Transfer Fluid; Reactor~170° C.; Hot Condenser~100° C.)

Equipment and procedures were identical to those described in Example 3 unless otherwise noted.

Approximately 131 g of mineral oil (MultiTherm PG-1® heat transfer fluid, MultiTherm® LLC, Malvern, Pa.) was added to the reactor. The autoclave temperature was maintained at 170° C. and the hot condenser was maintained at 100° C. Ammonium glycolate solution A was fed for 60 minutes and samples were combined like Example 2 to prepare samples "8A" and "8B". Results are summarized in Table 5.

EXAMPLE 5

Conversion of Ammonium Glycolate to Methyl Glycolate Using Heated Methanol Vapor as Esterifying Agent and Stripping Gas (Mineral Oil as Heat Transfer Fluid; Reactor~200° C.; Hot Condenser~130° C.)

Equipment and procedures were identical to those described in Example 2 unless otherwise noted.

Approximately 128 g of mineral oil (MultiTherm PG-1® heat transfer fluid, MultiTherm® LLC, Malvern, Pa.) was added to the reactor. The autoclave temperature was maintained at 200° C. and the hot condenser was maintained at 130° C. An ammonium glycolate solution (ammonium glycolate "solution B") was prepared by combining 75 g of glycolic acid crystals (99% glycolic acid, Sigma Aldrich Catalogue #124737) with 68.5 g of aqueous ammonium hydroxide solution (30 wt %, EMD Chemicals) and 25 g of deionized water. Ammonium glycolate solution B was fed for 50 minutes and samples were combined like Example 2 to prepare samples "9A" (collection time 0-25 min) and "9B" (collection time 25-50 min). Results are summarized in Table 5.

EXAMPLE 6

Conversion of Ammonium Glycolate to Methyl Glycolate Using Heated Methanol Vapor as Esterifying Agent and Stripping Gas (No High Boiling Point Fluid; Reactor~200° C.; Hot Condenser~130° C.)

Equipment and procedures were identical to Example 2 except no high boiling point fluid was used. Instead, the agitator was removed and 94 grams of packing material ("ProPak" ¼ inch high efficiency packing made from HASTELLOY® C276, Ace Glass Inc.) was added to the reactor (autoclave). The methanol feed line was inserted through the packing so methanol addition was at the bottom of the autoclave. An ammonium glycolate solution (ammonium glycolate "solution C") was prepared by combining equal mass of 70 wt % aqueous glycolic acid solution (Sigma Aldrich) and 30 wt% aqueous ammonium hydroxide solution (EMD Chemicals) followed by minor adjustments with GLA and ammonium to achieve a pH between 7.0 and 7.5. The ammonium glycolate feed was added to the top of the packing in the reactor.

The reactor temperature was maintained at 200° C. and the hot condenser was maintained at 130° C. Ammonium glycolate solution C was fed at 2.2 mL/minute for 60 minutes and samples were combined like Example 2 to prepare samples "11A" and "11B". Results are summarized in Table 5.

EXAMPLE 7

Conversion of Ammonium Glycolate to Methyl Glycolate Using Heated Methanol Vapor as Esterifying Agent and Stripping Gas (No Heat Transfer Fluid; Reactor~170° C.; Hot Condenser~100° C.)

Equipment and procedures were identical to Example 5 except the autoclave temperature was maintained at 170° C. and the hot condenser was maintained at 100° C. Ammonium glycolate "solution C" was fed for 60 minutes and samples were combined like Example 6 to prepare samples "13A" and "13B". Results are summarized in Table 5.

TABLE 5

Molar ratio of methanol, methyl glycolate, ammonium glycolate, and glycolic acid in samples from the hot condenser. Molar ratio calculated by standardizing methyl glycolate peak area to 1.

| Collection Time (minutes) | Sample Identification No. | Methanol (MeOH) | Methyl Glycolate (MeGLA) | Glycolic Acid (GLA) | Ammonium Glycolate (NH$_4$GLA) |
|---|---|---|---|---|---|
| 0-30 | 5A | 17.4 | 1.0 | 0.66 | 0.19 |
| 30-60 | 5B | 6.7 | 1.0 | 0.45 | 0.09 |
| 0-30 | 7A | 26.8 | 1.0 | 0.30 | 0.15 |
| 30-60 | 7B | 8.8 | 1.0 | 0.24 | 0.13 |
| 0-30 | 8A | 11.7 | 1.0 | 0.21 | 0.15 |
| 30-60 | 8B | 52.7 | 1.0 | 0.47 | 0.51 |

TABLE 5-continued

Molar ratio of methanol, methyl glycolate, ammonium glycolate, and glycolic acid in samples from the hot condenser. Molar ratio calculated by standardizing methyl glycolate peak area to 1.

| Collection Time (minutes) | Sample Identification No. | Methanol (MeOH) | Methyl Glycolate (MeGLA) | Glycolic Acid (GLA) | Ammonium Glycolate (NH₄GLA) |
|---|---|---|---|---|---|
| 0-25 | 9A | 12.8 | 1.0 | 0.49 | 0.15 |
| 25-50 | 9B | 6.1 | 1.0 | 0.47 | 0.17 |
| 0-30 | 11A | 70.6 | 1.0 | 1.18 | 0.24 |
| 30-60 | 11B | 26.6 | 1.0 | 0.59 | 0.16 |
| 0-30 | 13A | 27.4 | 1.0 | 0.26 | 0.17 |
| 30-60 | 13B | 17.9 | 1.0 | 0.19 | 0.17 |

What is claimed is:

1. A method to obtain a carboxylic acid ester from an aqueous solution of the carboxylic acid ammonium salt comprising
(a) providing
    (i) an aqueous solution comprising a carboxylic acid ammonium salt;
    said carboxylic acid ammonium salt having the formula:

$R_1-C(O)O^-NH_4^+$ or $NH_4^+{}^-O(O)C-R_1-C(O)O^-NH_4^+$ wherein $R_1$=C1 to C6 hydrocarbyl group independently selected from the group consisting of alkyl, cycloalkyl, and aryl; optionally substituted with at least one hydroxyl group; and
    (ii) a heated alcohol vapor feed stream comprising an alcohol having the formula:

$R_2-OH$ wherein $R_2$ is a C1 to C2 alkyl group; and
    (iii) a reaction vessel
(b) contacting said aqueous solution comprising carboxylic acid ammonium salt with said heated alcohol vapor feed stream in said reaction vessel whereby the heated alcohol vapor stream acts both as an esterifying agent and a stripping gas to produce a first vapor product stream comprising a carboxylic acid ester;
(c) separating within the reaction vessel the carboxylic acid ester from the aqueous solution; and
(d) recovering the carboxylic acid ester from said first vapor product stream using a condenser or a distillation column.

2. The method of claim 1 optionally comprising the step of hydrolyzing the carboxylic acid ester of (d) into the corresponding carboxylic acid.

3. The method of claim 2 further comprising the step of recovering the carboxylic acid.

4. The method according to claim 1 wherein the carboxylic acid ammonium salt is selected from the group consisting of ammonium acetate, ammonium propionate, ammonium butyrate, ammonium pentanoate, ammonium hexanoate, ammonium glycolate, ammonium lactate, diammonium adipate, diammonium succinate, diammonium glutarate, diammonium terephthalate, diammonium phthalate, and diammonium isophthalate.

5. The method according to claim 4 where the carboxylic acid ammonium salt is selected from the group consisting of ammonium lactate and ammonium glycolate.

6. The method according to claim 5 where the carboxylic acid ammonium salt is ammonium glycolate.

7. The method according to claim 1 wherein the ester is selected from the group consisting of acetic acid ester, propionic acid ester, butyric acid ester, pentanoic acid ester, hexanoic acid ester, glycolic acid ester, lactic acid ester, adipate acid diester, succinic acid diester, glutaric acid diester, terephthalic acid diester, phthalic acid diester, and isophthalic acid diester.

8. The method according to claim 7 where the ester is selected from the group consisting of lactic acid ester and glycolic acid ester.

9. The method according to claim 7 wherein the alcohol is methanol.

10. The method according to claim 9 wherein the ester is selected from the group consisting of methyl acetate, methyl propionate, methyl butyrate, methyl pentanoate, methyl hexanoate, methyl glycolate, methyl lactate, dimethyl adipate, dimethyl glutarate, dimethyl terephthalate, and dimethyl isophthalate.

11. The method according to claim 10 wherein the ester is methyl lactate or methyl glycolate.

12. The method according to claim 10 wherein the ester is methyl glycolate.

13. The method according to claim 3 wherein the carboxylic acid is selected from the group consisting of acetic acid, propionic acid, butyric acid, pentanoic acid, hexanoic acid, glycolic acid, lactic acid, adipic acid, glutaric acid, terephthalic acid, and isophthalic acid.

14. The method according to claim 13 wherein the carboxylic acid is selected from the group consisting of lactic acid and glycolic acid.

15. The method according to claim 13 wherein the carboxylic acid is glycolic acid.

16. The method according to claim 1 wherein the reaction vessel contains a non-reactive packing material and/or a high boiling point fluid.

17. The method according to claim 16 wherein the high boiling point fluid is selected from the group consisting of mineral oil and a polyol.

18. The method according to claim 17 wherein the polyol is selected from the group consisting of polyethylene ether glycol, polypropylene glycol, polytetramethylene glycol, decanol, dodecanol, and mixtures thereof.

19. The method according to claim 18 wherein the polyol is polytetramethylene ether glycol.

20. The method according to claim 1 wherein the temperature of the heated alcohol vapor is about 140° C. to about 350° C.

21. The method according to claim 20 wherein the alcohol is methanol and the temperature of the heated alcohol vapor is about 140° C. to about 300° C.

22. The method according to claim 1 wherein the reaction vessel temperature is about 140° C. to about 300° C.

23. The method according to claim 1 wherein the molar ratio of methanol to carboxylic acid ammonium salt is at least 5:1.

24. A method to produce glycolic acid ester from an aqueous solution comprising ammonium glycolate comprising:
(a) providing
    (i) an aqueous solution comprising ammonium glycolate; and
    (ii) a heated alcohol vapor feed stream comprising an alcohol having the formula:

$R_2-OH$ wherein R2 is a C1 to C4 straight chain or branched alkyl group; and (iii) a reaction vessel;

(b) contacting said aqueous solution comprising ammonium glycolate with said heated alcohol vapor feed stream in said reaction vessel whereby the heated alcohol vapor stream acts both as an esterifying agent and a stripping gas to produce a first vapor product stream comprising a glycolic acid ester;

(c) separating within the reaction vessel the glycolic acid ester from the aqueous solution; and (d) recovering the glycolic acid ester from said first vapor product stream using a condenser or a distillation column.

25. The method of claim 24 further comprising the step of hydrolyzing the glycolic acid ester of (d) into glycolic acid.

26. The method of claim 25 further comprising the step of recovering the glycolic acid.

27. The method according to claim 24 wherein the glycolic ester is selected from the group consisting of methyl glycolate, ethyl glycolate, propyl glycolate, and butyl glycolate.

28. The method according to claim 27 wherein the ester is methyl glycolate.

29. The method according to claim 24 where the alcohol is selected from the group consisting of methanol, ethanol, n-propanol, isopropanol, n-butanol, isobutyl alcohol, and t-butanol.

30. The method according to claim 29 wherein the alcohol is selected from the group consisting of methanol, ethanol, and n-propanol.

31. The method according to claim 30 wherein the alcohol is methanol.

32. The method according to claim 24 wherein the reaction vessel contains a non-reactive packing material and/or a high boiling point fluid.

33. The method according to claim 32 wherein the high boiling point fluid is selected from the group consisting of mineral oil and a polyol.

34. The method according to claim 33 wherein the polyol is selected from the group consisting of polyethylene ether glycol, polypropylene glycol, polytetramethylene glycol, decanol, dodecanol, and mixtures thereof.

35. The method according to claim 34 wherein the high boiling point fluid is polytetramethylene glycol.

36. The method according to claim 24 wherein the temperature of the heated alcohol vapor is about 170° C. to about 350° C.

37. The method according to claim 36 wherein the alcohol is methanol and the temperature of the heated alcohol vapor is about 170° C. to about 300° C.

38. The method according to claim 24 wherein the reaction vessel temperature is about 140° C. to about 300° C.

39. The method according to claim 24 wherein the molar ratio of methanol to ammonium glycolate is at least 5:1.

40. The method according to claim 1 or claim 24 wherein alcoholysis and recovery of the ester occurs in a single vessel.

41. The method of claim 1, wherein said aqueous solution of (a) comprises ammonium glycolate produced by enzymatic conversion of glycolonitrile.

42. The method of claim 24, wherein said ammonium glycolate is produced by enzymatic conversion of glycolonitrile.

* * * * *